(12) United States Patent
Gödiker et al.

(10) Patent No.: US 11,384,002 B2
(45) Date of Patent: Jul. 12, 2022

(54) PROCESS FOR PRODUCING A WORKPIECE WITH LOW TRANSLUCENCY

(71) Applicant: VITA ZAHNFABRIK H. RAUTER GMBH & CO. KG, Bad Säckingen (DE)

(72) Inventors: Michael Gödiker, Bad Säckingen (DE); Berit Müller, Bad Säckingen (DE); Jens Fischer, Bad Säckingen (DE); Wolfgang Rauh, Bad Säckingen (DE)

(73) Assignee: VITA ZAHNFABRIK H. RAUTER GMBH & CO. KG, Bad Saeckingen (DE)

( * ) Notice: Subject to any disclaimer, the term of this patent is extended or adjusted under 35 U.S.C. 154(b) by 201 days.

(21) Appl. No.: 15/767,436

(22) PCT Filed: Oct. 18, 2016

(86) PCT No.: PCT/EP2016/074946
§ 371 (c)(1),
(2) Date: Apr. 11, 2018

(87) PCT Pub. No.: WO2017/067909
PCT Pub. Date: Apr. 27, 2017

(65) Prior Publication Data
US 2018/0290913 A1    Oct. 11, 2018

(30) Foreign Application Priority Data
Oct. 19, 2015 (EP) .................................. 15190411

(51) Int. Cl.
*C03B 32/02* (2006.01)
*C03C 4/00* (2006.01)
(Continued)

(52) U.S. Cl.
CPC ................ *C03B 32/02* (2013.01); *A61K 6/16* (2020.01); *A61K 6/78* (2020.01); *A61K 6/816* (2020.01);
(Continued)

(58) Field of Classification Search
CPC ..... C03B 32/02; C03C 3/097; C03C 10/0027; C03C 3/083; C03C 4/0021
See application file for complete search history.

(56) References Cited

U.S. PATENT DOCUMENTS

2008/0120994 A1    5/2008  Schweiger et al.
2014/0141960 A1*   5/2014  Borczuch-Laczka .................. C03C 3/097
                                                                  501/32
(Continued)

FOREIGN PATENT DOCUMENTS

DE    261594 A1    11/1988
EP    1688398 A1    8/2006
(Continued)

OTHER PUBLICATIONS

Examination report issued in parallel Japanese Patent Application No. 2018-517401; dated Jun. 18, 2019; 5 pages.
(Continued)

*Primary Examiner* — Queenie S Dehghan
(74) *Attorney, Agent, or Firm* — Dilworth IP, LLC

(57) ABSTRACT

The present invention relates to a process for producing a workpiece made of glass ceramics, and to the workpiece obtainable by the process according to the invention. Further, the invention relates to the use of the workpiece obtained as a dental restoration, and to a process allowing the translucency of a workpiece to be controlled.

7 Claims, 1 Drawing Sheet

(51) Int. Cl.
   *C03C 3/083*   (2006.01)
   *C03C 10/00*   (2006.01)
   *C03C 3/097*   (2006.01)
   *A61K 6/16*    (2020.01)
   *A61K 6/78*    (2020.01)
   *A61K 6/816*   (2020.01)
   *A61K 6/822*   (2020.01)
   *A61K 6/827*   (2020.01)
   *A61K 6/833*   (2020.01)

(52) U.S. Cl.
   CPC .............. *A61K 6/822* (2020.01); *A61K 6/827* (2020.01); *A61K 6/833* (2020.01); *C03C 3/083* (2013.01); *C03C 3/097* (2013.01); *C03C 4/0021* (2013.01); *C03C 10/0027* (2013.01)

(56) References Cited

U.S. PATENT DOCUMENTS

2014/0252272 A1   9/2014   Durschang et al.
2015/0274580 A1*  10/2015  Vollmann ................ C03C 3/097
                                                           501/32

FOREIGN PATENT DOCUMENTS

| EP | 2944619 A1 | 11/2015 |
| JP | H06279054 A | 10/1994 |
| JP | 2013515659 A | 5/2013 |
| WO | 87/07256 A1 | 12/1987 |
| WO | 2014/177659 A1 | 11/2014 |

OTHER PUBLICATIONS

PCT International Search Report and Written Opinion dated Feb. 10, 2017 from Application No. PCT/EP2016/074946, 18 pages.

* cited by examiner

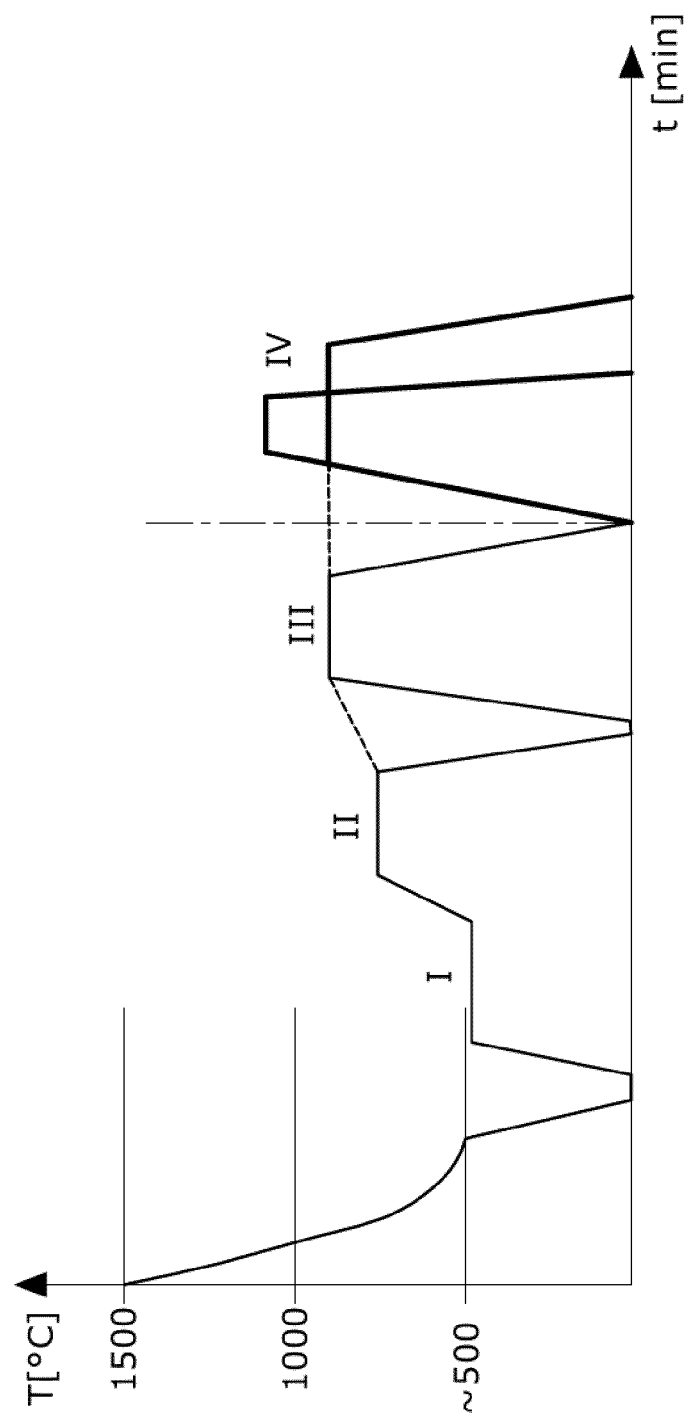

PROCESS FOR PRODUCING A WORKPIECE WITH LOW TRANSLUCENCY

FIELD OF THE INVENTION

The present invention relates to a process for producing a workpiece made of glass ceramics, and to the workpiece obtainable by the process according to the invention. Further, the invention relates to the use of the workpiece obtained as a dental restoration, and to a process allowing the translucency of a workpiece to be controlled.

BACKGROUND OF THE INVENTION

Because of the continuous further development in the field of dentistry, there is an increasing need for materials that can be processed to dental restorative products, such as crowns or inlays. In addition to health safety, suitable materials must have further properties allowing them to be used as a dental restoration. On the one hand, the materials must have a high strength and chemical resistance, so that they can adopt the function of the natural tooth material, being adequate to the high mechanical load that arises during the chewing process, in particular. In addition, these properties must be maintained over a sufficiently long period of time while the material is in permanent contact with in part aggressive liquids, which may be acidic, for example.

In addition to the mechanical requirements, the focus is on the optical properties, above all. Ideally, a dental restoration is characterized by appealing optical properties, such as translucency and color, which come as close as possible to the appearance of natural teeth. This is difficult, in particular, in cases where the restoration is to be applied to the existing dental material, for example, to tooth stumps.

Most dental materials are matched to a healthy remaining tooth structure, which does not reflect reality in most cases, however. Rather, the remaining tooth structure is mostly devitalized or discolored from former fillings, whereby the color effect of the restoration attached thereto may be adversely affected.

Although a higher opacity, i.e., a low light transmittance, can be achieved by a corresponding turbidity of the material, there is a very fine line between a restoration giving a "natural" or a "dead" impression, and matching the respective patient's case is only coarsely possible.

One possibility to meet the above described problems is to use masking fixing materials in order to conceal dark stumps. However, this leads to a blocking of the optical properties of the natural stump. Other proposals for solving the mentioned problems include, for example, the use of glass infiltration ceramics, such as In-Ceram Zirconia, veneered $ZrO_2$ scaffolds, or opaque variants of such materials, wherein in these cases the amount of additives used for adjusting the opacity often has the effect that the latter form a separate phase in the material, whereby the mechanical properties deteriorate.

The general knowledge of the art is represented for example by Borom et al.: Strength and Microstructure in Lithium Disilicate Glass-Ceramics, Journal of the American Ceramic Society, Vol. 58, pp. 385 to 391, incorporated by reference.

DE 103 36 913 describes a process for producing a lithium silicate ingot, in which the ingot is subjected to a two-step thermal treatment.

DE 10 2010 050 275 describes a glass ceramic based on the lithium metasilicate system ($Li_2O*SiO_2$ ($Li_2SiO_3$)), which can be readily processed mechanically in an intermediate stage of crystallization, and forms a chemically stable glass ceramic of high strength and high translucency after crystallization is complete.

EP 2 944 619 A1 discloses a method for producing a lithium silicate glass or a lithium silicate glass ceramic containing cerium ions and which is particularly suitable for the production of dental restorations whose fluorescence properties substantially correspond to those of natural teeth. Also described are a lithium silicate glass and a lithium silicate glass ceramic obtainable by the method according to the invention, which are suitable for use as dental material and particularly for the production of dental restorations, and a glass-forming composition which is suitable for use in the method according to the invention.

WO 2014/177656 A1 discloses an ingot for producing a dental shaped body, such as an inlay, onlay, crown or bridge, and to a method for producing the ingot. In order that a dental shaped body, especially one with a thin wall thickness, can be processed without difficulty from the ingot, it is provided that the ingot is made of a glass ceramic with a density of from 30% and 60% of the theoretical density and of glass powder particles having a grain size distribution of d90<80 μm, the proportion of lithium silicate being 10% by volume to 90% by volume.

WO 87/07256 A1 discloses a machinable glass ceramic that also has other good characteristics, such as hardness, chemical durability and biocompatibility, is formed from a batch mix having the composition range (in mole %): $Al_2O_3$: 1.5 to 15.0; CaO: 22.0 to 55.0; $P_2O_5$: 28.0 to 65.0; $SiO_2$ (and/or $B_2O_3$): up to 15.0; $TiO_2$ (and/or $ZrO_2$): up to 10.0. Up to 15 mole % may be added of any one or more of $Na_2O$, $K_2O$, $Li_2O$, MgO, BaO and ZnO, to aid melting of the glass. Specific manufacturing stages and two specific batch mixes are given, and a wide range of uses is suggested.

EP 1 688 398 A1 discloses lithium silicate materials which can be easily processed by machining to dental products without undue wear of the tools and which subsequently can be converted into lithium silicate products showing high strength.

However, none of the processes described in the prior art is suitable for providing a restoration with the appropriate optical properties that in addition can be adapted individually to the needs of the patient directly in the dentist's practice and thus enables a so-called dentist treatment "chair-side".

SUMMARY OF THE INVENTION

It is the object of the present invention to provide a process and a workpiece by which the mentioned drawbacks are overcome.

According to the invention, this object is achieved by a process for producing a workpiece made of glass ceramics, comprising the following steps:
a) a first thermal treatment of the workpiece at a first temperature $T_1$ within a range of from 400 to 700° C. for a period of 10 to 180 minutes;
b) a second thermal treatment of the workpiece at a second temperature $T_2$ within a range of from 500 to 800° C. for a period of 10 to 400 minutes, the second temperature $T_2$ being higher than the first temperature $T_1$;
c) a third thermal treatment of the workpiece at a third temperature $T_3$ within a range of from 600 to 1100° C. for a period of 2 to 90 minutes, the third temperature $T_3$ being higher than the temperature $T_1$ and the temperature $T_2$;

d) cooling the workpiece down to a temperature $T_{cool}$, which is below the glass transition temperature of the glass ceramic;

characterized in that e) there is a fourth thermal treatment of the workpiece at a fourth temperature $T_4$ within a range of from 600 to 1100° C. for a period of 2 to 30 minutes, the temperature $T_4$ being higher than the temperature $T_1$ and the temperature $T_2$; and wherein after the end of the fourth thermal treatment f) cooling of the workpiece to a temperature $T_f$ as desired by the user is effected.

Surprisingly, it has been found that an optical matching of the dental restoration to the patient's remaining teeth is enabled by subjecting the workpiece to another thermal treatment that follows the treatments usual in the prior art. Further, it has surprisingly been found that the additional thermal treatment may additionally improve the mechanical properties, especially the biaxial strength, of the workpiece, and that the workpiece obtained accordingly meets the requirements demanded of a dental restoration.

BRIEF DESCRIPTION OF THE DRAWINGS

FIG. 1 schematically shows the temperature course of the process according to the invention for producing a workpiece made of glass ceramics, the temperature levels of the individual thermal treatments being designated accordingly (I to IV).

DETAILED DESCRIPTION OF THE INVENTION

In particular, the glass ceramic may be selected from the group consisting of lithium silicate glass ceramics, leucite glass ceramics, and feldspar glass ceramics. In the following, the invention is explained in more detail by the example of the lithium silicate glass ceramics.

In a preferred embodiment, the individual thermal treatments are performed in one or more furnaces, wherein the furnaces in which the individual treatment steps are performed may be different. More preferably, steps a) and b) of the process according to the invention are performed in a different furnace than that used in the following steps c) to e). This process control mode allows the workpiece to be processed directly in the dentist's practice, so that a matching to the patient's individual needs can be effected in an optimized way (treatment on the chair). Therefore, in a particular embodiment, the process according to the invention is a batch process.

Typically, the duration of the individual thermal treatments is 1 to 360 minutes each, especially 3 to 360 minutes, and specifically 5 to 360 minutes. Surprisingly, it has been found that particularly good optical properties could be achieved in this way. When the duration of the treatments was outside the stated ranges, the optical and mechanical properties were inadequate, and for example, the dental restorations obtained were not suitable for application to previously discolored tooth stumps.

In order to form the workpiece into the desired shape, the workpiece is typically cooled down between steps b) and c) of the process, especially to room temperature. Suitable processing methods include mechanical processing methods, for example, CAD/CAM methods, by which the workpiece can be formed into the shape of a dental restoration, for example.

The adjusting of the optical properties of the workpiece in order to achieve as exactly as possible a matching of the color to that of the natural teeth may require a precise tuning of the temperature and the duration of the thermal treatment. Inter alia, the starting temperature and the heating rate are also to be taken into account in order to avoid too great a load on the workpiece from temperature variations and differences that may occur. Therefore, an embodiment is particularly suitable in which the temperature $T_1$ of the first thermal treatment is reached from room temperature or from a pretreatment temperature of from 300° C. to 600° C. Further, an embodiment is preferred in which the heating rate of the first thermal treatment is from 1° C./min to 100° C./min, especially from 2° C./min to 50° C./min.

Typically, the temperature $T_1$ of the first thermal treatment is selected to be within the range of the nucleation temperature of the glass ceramics. In particular, in the case of lithium silicate glass ceramics, the temperature $T_1$ is selected to induce the formation of lithium metasilicate nuclei in the glass ceramics.

In another suitable embodiment, the temperature $T_2$ of the second thermal treatment is reached from room temperature or from a pretreatment temperature of from 500° C. to 800° C. In particular, the heating rate of the second thermal treatment may be from 1° C./min to 100° C./min, especially from 2° C./min to 50° C./min.

The temperature $T_2$ of the second thermal treatment is higher than that of the first thermal treatment. Advantageously, the temperature $T_2$ is selected to promote the grain growth of the glass ceramics, especially the growth of the nuclei formed during the first thermal treatment.

The temperature $T_3$ of the third thermal treatment may be reached from room temperature or from a pretreatment temperature of from 700° C. to 900° C. The heating rate is typically from 1° C./min to 100° C./min, especially from 2° C./min to 50° C./min.

Further, the temperature $T_4$ of the fourth thermal treatment may be reached from room temperature or from a pretreatment temperature of from 750° C. to 890° C. The heating rate of the fourth thermal treatment is typically from 1° C./min to 100° C./min, especially from 2° C./min to 50° C./min.

In particular, the temperature $T_3$ of the third thermal treatment is selected to induce the formation of the final crystal phases in the glass ceramics. Suitably, the temperature is within a range of from 650 to 1000° C., especially within a range of from 700 to 900° C.

The process according to the invention allows a workpiece to be produced in which the optical and mechanical properties can be influenced by a number of thermal treatments. Surprisingly, it has been found that the optical and mechanical properties of the workpiece can be influenced positively especially by a further thermal treatment after the formation of the crystal phases. Therefore, the process according to the invention is characterized by an additional thermal treatment step at a temperature $T_4$. Typically, the temperature $T_4$ of the fourth thermal treatment may be within a range of from 650 to 1000° C., especially from 700 to 900° C. Surprisingly, it has been found that the optical properties of the workpiece, in particular, can be controlled by this further thermal treatment, and that darker shades, in particular, are accessible in this way.

The workpiece obtainable by the process according to the invention may be processed mechanically between the individual process steps to form it into the desired shape, for example, by means of computer-aided machining e.g. milling or grinding methods, especially CAD/CAM methods. Therefore, the workpiece is typically an ingot or a shaped workpiece.

As set forth above, the workpiece obtainable by the process according to the invention has excellent optical and mechanical properties, as required in the field of dental restorations, in particular. Therefore, an embodiment is particularly suitable in which the shaped workpiece is a dental restoration. Said dental restoration is, for example, in the form of an inlay, onlay, bridge, post construction, veneer, shell, facet, crown, partial crown, scaffold or cap.

For dental restorations, lithium silicate glass ceramics, above all, have proven particularly suitable. Therefore, in a typical embodiment, the ingot is obtained from a starting melt comprising the following components:

55-64% by weight $SiO_2$,
10-20% by weight $Li_2O$,
8-20% by weight of a stabilizer,
0-5% by weight $K_2O$,
0.1-5% by weight $Al_2O_3$, and
0-10% by weight additives, wherein the percentages by weight are respectively based on the total weight of the starting melt.

In particular, the stabilizer is selected from the group consisting of $ZrO_2$, $HfO_2$ and mixtures thereof. Against expectations, it has been found that the $ZrO_2$ does not crystallize as its own crystal phase, but remains in the amorphous residual glass phase, even if the $ZrO_2$ is employed in an amount of up to 20% by weight, based on the total weight of the starting melt. Surprisingly, it has been found that the mechanical and chemical resistance can be improved by the presence of the stabilizer, which is manifested, inter alia, in an increased final strength and a lower acid solubility of the glass ceramics.

The additives that may be contained in the starting melt are selected, for example, from the group consisting of nucleating agents, colorants, especially glass-coloring oxides and/or pigments.

In particular, the glass-coloring oxides are selected from the group of oxides of iron, titanium, cerium, copper, chromium, cobalt, nickel, manganese, selenium, silver, indium, gold, rare earth metals, especially neodymium, praseodymium, samarium and europium, and mixtures thereof.

The pigments are typically doped spinels.

Suitable oxides, such as phosphorus oxide, titanium oxide, zirconium oxide or tin oxide, are employed as nucleating agents, in particular. Further additives are, for example, selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide, and mixtures thereof.

The conditions under which the individual thermal treatment steps of the process according to the invention are effected may be adapted individually to the local circumstances and needs. Thus, for example, the thermal treatments may be performed under an inert gas atmosphere or under reduced pressure. Therefore, an embodiment of the process is particularly suitable in which one or more of the temperature treatments, typically the third and/or fourth, are performed in the presence of an inert gas.

Further suitable is an embodiment of the process in which one or more of the temperature treatments are performed in a furnace, and wherein the pressure within the furnace is lower than the pressure outside the furnace.

The present invention further relates to a workpiece obtainable by the process according to the invention.

As set forth above, the optical properties of the workpiece are important, above all. These are primarily determined by the transmission, hereinafter also referred to as translucency, of the workpiece. The lower the light transmission of the workpiece, the darker the color appears. In order to be able to imitate the appearance of a natural tooth, the workpiece should have a translucency of above 5%, the translucency reflecting the ratio of light intensity behind (I) and in front of the workpiece ($I_0$). In a particular embodiment, the workpiece has a translucency within a range of from 5 to 70%, especially as measured over the entire spectrum of wavelengths from 360 to 740 nm and at a layer thickness of 1 mm.

The workpiece according to the invention is further characterized by a high strength and chemical stability, which allows it to be used as a dental restoration, being adequate to the mechanical stresses, for example, during the chewing process, and to the aggressive environment in the oral cavity. Therefore, in a preferred embodiment, the workpiece has a biaxial strength within a range of at least 200 MPa, especially from 300 to 650 MPa, especially from 320 to 600 MPa, as determined according to DIN EN ISO 6872.

Lithium silicate glass ceramics are characterized by a high workability and at the same time a high mechanical strength. Therefore, an embodiment is preferred in which the workpiece is lithium silicate glass ceramics.

Surprisingly, it has been found that the workability of lithium silicate glass ceramics can be improved if the glass ceramics have some proportion of lithium metasilicate without the strength being influenced. Therefore, an embodiment of the workpiece is preferred in which the workpiece contains at least 10% by weight lithium metasilicate, preferably at least 50% by weight. More preferably, the workpiece contains from 20 to 40% by weight lithium metasilicate, as measured by means of XRD analysis.

The workpiece according to the invention is characterized by excellent optical and mechanical properties, which are important in dental restorations, in particular. Therefore, the present invention further relates to the use of the workpiece according to the invention as a dental restoration.

Especially in the field of tooth preservation or tooth replacement, it is important that the inserted dental restorations are optically matched to the remaining teeth in order to achieve as natural as possible an appearance. The optical properties, especially the color of the individual restorations, can be controlled via their translucency. Thus, restorations with a low translucency, appear more opaque, i.e., less transparent.

Within the scope of the present invention, it has surprisingly been found that the translucency of a workpiece can be influenced by the duration and number of thermal treatments and their temperatures. Therefore, the present invention further relates to the use of the process according to the invention for controlling the translucency of a workpiece made of lithium silicate glass ceramics.

Further, it has surprisingly been found that the formation of the lithium disilicate phase in the glass ceramics, in particular, determines the translucency. Therefore, the present invention further relates to a process for controlling the translucency of a workpiece made of lithium silicate glass ceramics, wherein the translucency is controlled by the duration of the thermal treatment for the formation of the lithium disilicate phase.

Surprisingly, it has been found that the process according to the invention allows workpieces with a low translucency to be produced, in particular. Therefore, an embodiment is preferred in which the translucency decreases in the course of the thermal treatment.

The process for producing a workpiece made of glass ceramics according to the present invention has proven particularly suitable for adjusting the translucency of a workpiece made of lithium silicate glass ceramics, especially in cases where said glass ceramics are lithium silicate glass ceramics. Surprisingly, it has been found that a significant decrease of transmission can be achieved especially by the fourth thermal treatment as compared to workpieces in which such a thermal treatment has not been effected. The translucencies achieved by the process according to the invention are typically by 20 to 50% below those found for a workpiece produced by a conventional process, i.e., without a fourth thermal treatment. Thus, the translucency can be varied by up to 50%, in particular, as compared to workpieces which have not been subjected to a fourth thermal treatment.

The present invention is to be described further by means of the following Examples, which are not to be understood as limiting the spirit of the invention.

All references cited herein are incorporated by reference to the full extent to which the incorporation is not inconsistent with the express teachings herein.

Examples

Different thermal treatments were performed, the starting melt having the following composition: 60% by weight $SiO_2$, 19% by weight $Li_2O$, 10% by weight $ZrO_2$, 6% by weight $P_2O_5$, 2% by weight $Al_2O_3$, 2% by weight $K_2O$, and 1% by weight $CeO_2$.

Thermal Treatments:

Performance: The first two temperature treatments were performed at a production scale in a convection oven. The hold times and heating rates were selected to obtain a homogeneous heat distribution. The third and fourth temperature treatments were performed in a dental furnace.

TABLE 1

| Example | $T_1$ [° C.]/ duration [min] | $T_2$ [° C.]/ duration [min] | $T_3$ [° C.]/ duration [min] | $T_{cool}$ [° C.] | $T_4$ [° C.]/ duration [min] |
|---|---|---|---|---|---|
| 1 | 550/60 | 650/90 | 840/8 | — | — |
| 2 | 550/60 | 650/90 | 840/8 | 400 | 840/8 |
| 3 | 550/60 | 650/90 | 840/8 | 400 | 840/4 |
| 4 | 550/60 | 650/90 | 840/8 | 400 | 820/16 |
| 5 | 550/60 | 650/90 | 840/8 | 400 | 860/4 |

Heating Rates:
first and second thermal treatment: 2-10 K/min
third and fourth thermal treatment: 40-80 K/min In a further step, the translucency and the biaxial strength of the glass ceramics obtained were determined.

The translucency was determined as follows:
Measuring device: X-Rite Color Master
Measuring aperture: SAV (Ø 10 mm)
Light type: D65
Observer: 10°
Sample thickness: 1.0 mm The stated translucency corresponds to the average over the different wavelength ranges.

The biaxial strength was determined according to DIN EN ISO 6872.

TABLE 2

| Example | Biaxial strength [MPa] | St. Dev.[a] | Translucency [%] | L* | a* | b* | Δ Translucency[b] |
|---|---|---|---|---|---|---|---|
| 1 (comparative) | 274.95 | 78.25 | 28.21 | 62.70 | 3.57 | 30.34 | — |
| 2 | 328.51 | 66.03 | 16.66 | 47.68 | 10.83 | 49.12 | −40% |
| 3 | 388.93 | 69.53 | 21.11 | 54.74 | 7.16 | 41.24 | −25% |
| 4 | 404.49 | 54.50 | 17.21 | 48.40 | 10.79 | 49.02 | −39% |
| 5 | 395.54 | 33.96 | 17.04 | 48.39 | 9.63 | 45.41 | −40% |

[a]Standard deviation
[b]The differences in translucency were determined by comparing the values of the Comparative Example with those of the Examples according to the invention, wherein the value of the translucency of the Comparative Example was assumed to be 100%.

As can be seen from Table 2, the sample of the Comparative Example 1, in which the workpiece was not subjected to any additional thermal treatment, as usual in the prior art, has a lower biaxial strength as compared to the samples of Examples 2 to 5, which were prepared by the process according to the invention.

Further, it can be seen from Table 2 that the translucency decreases, i.e., the workpiece appears more opaque, as the temperature or duration of thermal treatment increases.

As demonstrated by the provided Examples, the process according to the invention enables workpieces made of glass ceramics to be produced that are characterized by an increased strength. Further, the additional thermal treatment enables the translucency of the workpiece to be controlled by adapting the temperature and duration of the thermal treatment. Thus, the translucency can be varied by 50% as compared to workpieces that were not subjected to a fourth thermal treatment.

We claim:

1. A process for producing a dental restoration made of glass ceramics, comprising the following steps in the order:
   a) a first thermal treatment of a workpiece at a first temperature $T_1$ within a range of from 400 to 700° C. for a period of 10 to 180 minutes;
   b) a second thermal treatment of the workpiece at a second temperature $T_2$ within a range of from 500 to 800° C. for a period of 10 to 400 minutes, the second temperature $T_2$ being higher than the first temperature $T_1$;
   b-1) cooling the workpiece to room temperature and forming the workpiece to a dental restoration;
   c) a third thermal treatment of the dental restoration at a third temperature $T_3$ within a range of from 600 to 1100° C. for a period of 2 to 90 minutes for forming the final crystal phase of the dental restoration, the third temperature $T_3$ being higher than the temperature $T_1$ and the temperature $T_2$;
   d) cooling the dental restoration down to a temperature $T_{cool}$, which is below the glass transition temperature of the glass ceramic after the third heat treatment;
   characterized in that
   e) there is a fourth thermal treatment of the dental restoration, after the cooling step d), at a fourth temperature $T_4$ within a range of from 600 to 1100° C. for a period of 2 to 30 minutes, the temperature $T_4$ being higher than the temperature $T_1$ and the temperature $T_2$; and
   wherein after the fourth thermal treatment,
   f) cooling of the dental restoration to a temperature $T_f$ as desired by the user is effected,
   wherein the dental restoration is obtained from a starting melt comprising 55-64% by weight $SiO_2$, 10-20% by weight $Li_2O$, 8-20% by weight of a stabilizer, 0-5% by weight $K_2O$, 0.1-5% by weight $Al_2O_3$, and 0-10% by weight additives, based on the total weight of the starting melt, and there is no change in the crystalline phase of the workpiece after the fourth heat treatment of step e) relative to the crystalline phase present after the third thermal treatment in step c).

2. The process according to claim 1, characterized in that the temperature $T_4$ of the additional thermal treatment is reached from room temperature or from a pretreatment temperature of from 750° C. to 890° C.

3. The process according to claim 1, characterized in that the temperature $T_3$ of the third thermal treatment is within a range of from 650 to 1000° C.

4. The process according to claim 3 wherein the range of $T_3$ is 700 to 900° C.

5. The process according to claim 1, characterized in that the temperature $T_4$ of the fourth thermal treatment is within a range of from 650 to 1000° C.

6. The process according to claim 5 wherein the range of $T_4$ is 700 to 900° C.

7. The process according to claim 1 wherein the $SiO_2$ content is from 55% to 60% by weight.

* * * * *